United States Patent [19]

Greber et al.

[11] Patent Number: 5,288,876
[45] Date of Patent: Feb. 22, 1994

[54] BENZOPHENONE IMINODIIMIDES AND HEAT-STABLE POLYMERS DERIVED THEREFROM

[75] Inventors: Gerd Greber, Bad Vöslau; Heinrich Gruber; Afschin Hassanein, both of Vienna, all of Austria

[73] Assignee: Chemie Linz Gesellschaft G.m.b.H., Linz, Austria

[21] Appl. No.: 916,749

[22] Filed: Jul. 22, 1992

[30] Foreign Application Priority Data

Aug. 13, 1991 [AT] Austria .................................. 1590/91

[51] Int. Cl.$^5$ ............................................. C07D 403/06
[52] U.S. Cl. ..................................... 548/455; 548/461
[58] Field of Search ................................... 548/461, 455

[56] References Cited

U.S. PATENT DOCUMENTS

| | | | |
|---|---|---|---|
| 3,847,870 | 11/1974 | Takekoshi | 260/47 CP |
| 3,855,178 | 12/1974 | White et al. | 260/45.7 S |
| 3,895,064 | 7/1975 | Brode et al. | 260/571 |
| 3,905,942 | 9/1975 | Takekoshi et al. | 260/47 CP |
| 3,992,407 | 11/1976 | Markezich | 260/326 W |
| 4,045,407 | 8/1977 | Keske et al. | 260/47 CP |
| 4,131,610 | 12/1978 | Audeh | 260/326 N |
| 4,194,885 | 3/1980 | Audeh | 44/63 |

FOREIGN PATENT DOCUMENTS

| | | |
|---|---|---|
| 0162606 | 11/1985 | European Pat. Off. |
| 0077834 | 12/1985 | European Pat. Off. |
| 0252415 | 1/1988 | European Pat. Off. |
| 1393298 | 5/1975 | United Kingdom |
| 2035295 | 6/1980 | United Kingdom |

OTHER PUBLICATIONS

Chemical Abstracts, 102:221314g (1985).
Chemical Abstracts, 104:199007f (1986).
Chemical Abstracts, 82:157200f (1975).
Chemical Abstracts, 86:6105k (1977).
*Macromolecules*, 21(7) 1929-1935 (1988).
Chemical Abstracts, 104:186134r (1986).
Chemical Abstracts, 109:38328v (1988).
Chemical Abstracts, 104:186134r (1986).
Chemical Abstracts, 110:97050s (1989).
Mosher et al., "J. Heterocycl. Chem.", 9 319-324 (1972).

*Primary Examiner*—David B. Springer
*Attorney, Agent, or Firm*—Wenderoth, Lind & Ponack

[57] ABSTRACT

Benzophenone iminodiimides of the formula I

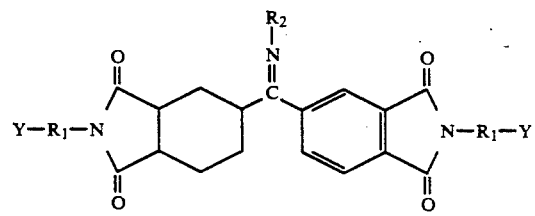

in which Y denotes hydroxyl or carboxyl, $R_1$ denotes the optionally substituted radicals alkylene, phenylene or benzylidene, $R_2$ denotes the radicals OH, substituted or unsubstituted alkyl or NH—CO—NHR$_3$ and $R_3$ denotes the radicals H, alkyl, phenyl or benzyl, processes for their preparation and polymers prepared therefrom.

3 Claims, No Drawings

BENZOPHENONE IMINODIIMIDES AND HEAT-STABLE POLYMERS DERIVED THEREFROM

The invention relates to benzophenone iminodiimides and heat-stable polymers derived therefrom.

The heat-stable polymers which are to date the most important industrially are completely aromatic polyimides, polyamides and polyamide-imides. Although polyimides have an extremely high heat stability, they are usually neither fusible nor soluble and can therefore be processed only with effort and expense. The somewhat less heat-stable aromatic polyamides are also non-fusible and insoluble or only slightly soluble in most organic solvents, so that their processing from solutions to give fibers or films is associated with great difficulties. Although the solubility and processability of aromatic polymers is improved by incorporation of diamines or dianhydrides having flexible chain elements (—CH—, —O—, —S— or —CO—) or of sterically demanding diamines, as described in EP-A-0,162,606 and U.S. Pat. No. 3,895,064, the heat stability is significantly reduced.

New monomers based on 3,3',4,4'-benzophenonetetracarboxylic acid dianhydride (BTDA) by incorporation of azomethine groups have now been found, which lead to polymers of high heat stability, good solubility, low glass transition temperatures and easy thermoplastic processability.

The present invention accordingly relates to benzophenone iminodiimides of the formula I

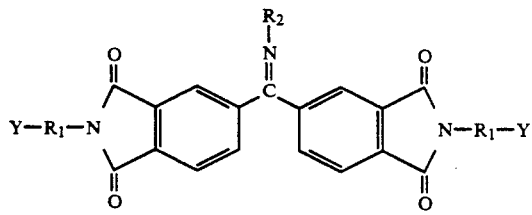

in which Y denotes hydroxyl or carboxyl, $R_1$ denotes a straight-chain or branched alkylene radical having 1 to 6 C atoms, or an o-, m- or p-phenylene or benzylidene radical which is optionally substituted by Cl, lower alkyl or lower alkoxy, and $R_2$ denotes the radical OH, a straight-chain or branched, saturated or mono- or polyunsaturated alkyl radical having 1 to 20 C atoms, which can be substituted by Cl, OH, $NH_2$, $CONH_2$ or $COOR_3$, or a radical of the formula NH—CO-NHR$_3$, wherein $R_3$ can be hydrogen, an alkyl radical having 1 to 4 C atoms or a phenyl or benzyl radical.

In formula I, $R_1$ denotes a straight-chain or branched alkylene radical having 1 to 6 C atoms, such as, for example, a methylene, ethylene, propylene, isopropylene, butylene, sec-butylene or hexylene radical, or an o-, m- or p-phenylene or benzylidene radical which is unsubstituted or substituted by Cl, lower alkyl groups having 1 to 5 C atoms, such as, for example, methyl, ethyl or propyl groups, or lower alkoxy groups having 1 to 5 C atoms, such as, for example, methoxy, ethoxy or propoxy groups, and $R_2$ denotes the radical OH, or a straight-chain or branched, saturated or mono- or polyunsaturated alkyl radical which has 1 to 20 C atoms and is unsubstituted or substituted by OH, Cl, $NH_2$, $CONH_2$ or $COOR_3$, such as, for example, a methyl, ethyl, hexyl, dodecyl, octadecyl, vinyl, allyl, butadienyl, isoprenyl, hydroxyethyl, hydroxyhexyl, hydroxydodecyl, hydroxyoctadecyl, carboxymethyl, carboxyethyl, carboxydodecyl, carboxyoctadecyl, carboxyhexadecenyl, aminohexyl, aminododecyl or aminotridecenyl radical, or a radical of the formula —NH—CO—NHR$_3$, such as, for example, semicarbazyl, methylsemicarbazyl, ethylsemicarbazyl, phenylsemicarbazyl or benzylsemicarbazyl. $R_3$ denotes hydrogen or an alkyl radical having 1 to 4 C atoms, such as, for example, a methyl, ethyl or propyl radical.

Preferred compounds of the formula I are those in which $R_1$ denotes a straight-chain alkylene radical having 1 to 4 C atoms, such as, for example, a methylene, ethylene or butylene radical, or an m- or p-phenylene or benzylidene radical which is unsubstituted or substituted by lower alkyl or lower alkoxy groups having 1 to 4 C atoms, such as, for example, methyl, ethyl, propyl, methoxy, ethoxy or propoxy groups, and $R_2$ denotes the radical OH, or a straight-chain, saturated alkyl radical which has 1 to 18 C atoms and is unsubstituted or substituted by OH, $NH_2$ or COOH, such as, for example, a methyl, ethyl, hexyl, dodecyl, octadecyl, hydroxyethyl, hydroxyhexyl, carboxymethyl, carboxyethyl, carboxyoctadecyl, aminoethyl or aminohexyl radical, or a semicarbazyl or phenylsemicarbazyl radical.

Particularly preferred compounds of the formula I are those in which R denotes an ethylene or unsubstituted p-phenylene radical and $R_2$ denotes the radical OH, or a straight-chain, saturated alkyl radical which has 1 to 8 C atoms and is unsubstituted or substituted by OH, $NH_2$ or COOH, such as, for example, a methyl, ethyl, propyl, hexyl, hydroxyethyl, hydroxyhexyl, carboxymethyl, carboxyethyl, aminomethyl, aminoethyl or aminohexyl radical, or a semicarbazyl or phenylsemicarbazyl radical.

The present invention furthermore relates to a process for the preparation of compounds of the formula I

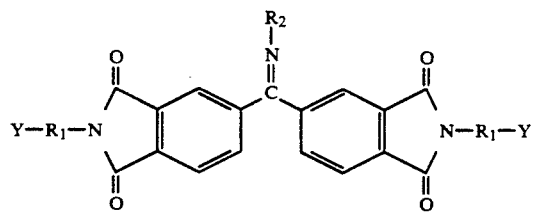

in which Y, $R_1$, $R_2$ and $R_3$ are as defined above, which is characterized in that compounds of the formula II

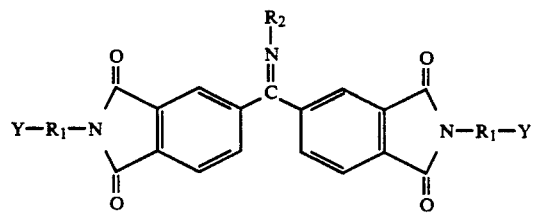

in which R and Y are as defined above, are reacted with compounds of the formula III $R_2$—$NH_2$ in which $R_2$ is as defined above.

The benzophenonetetracarboxylic acid diimide (BTDI) derivatives of the formula II employed as starting compounds can be prepared as described, for example, in Mosher W.A.K., Chlystek, S., J. Heterocycl. Chem. Volume 9, (1972) page 319 by reaction of BTDA with an equimolar amount of an aminoalcohol or an aminocarboxylic acid, such as, for example, ethanolamine, p-aminophenol or p-aminobenzoic acid.

The BTDI derivatives are then reacted with amines of the formula III to give the desired benzophenone iminodiimides (Schiff's bases).

1 to 10 moles, preferably 1.05 to 5 moles, of amine of the formula III are employed per mole of BTDI derivative.

Amines of the formula III are, for example, n-hexylamine, hydrazine, glycine, hydroxylamine, ethanolamine, semicarbazide, phenylsemicarbazide, hexamethylenediamine, aminopalmitic acid or aminostearic acid.

The reaction is preferably carried out in a diluent which is inert under the reaction conditions, such as, for example, dimethylacetamide (DMA), dimethylformamide (DMF), N-methylpyrrolidone (NMP), dimethyl sulfoxide (DMSO), tetramethylurea or hexamethylphosphoric acid triamide (HMP).

DMA is preferably employed as the diluent. Small amounts, for example 0.01 mol, of a catalyst, such as, for example, toluenesulfonic acid, acetic acid, a mineral acid or an acid ion exchanger, can be added to the reaction mixture of the BTDI derivative and amine. The water formed during the reaction is advantageously removed by azeotropic distillation with a solvent which is inert under the reaction conditions, such as, for example, benzene or toluene. If appropriate, the excess amine can be recovered by distillation or recrystallization, or also as a salt. It is also possible to employ salts of the amines, such as, for example, hydroxylamine hydrochloride. DMA/water mixtures can also be used as the diluent, from which the desired compound is then precipitated. The Schiff's bases according to the invention can be isolated by customary methods, such as, for example, crystallization, extraction or precipitation, depending on their physical properties.

If necessary, the crude products isolated in this way can then be further purified by known methods, such as, for example, recrystallization, reprecipitation or chromatography.

The Schiff's bases according to the invention can then be used for the preparation of polymers.

The present invention accordingly furthermore relates to polyesters of the formula IVa

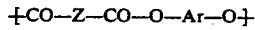

or IVb

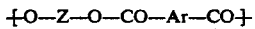

in which Z denotes a substituted or unsubstituted, straight-chain or branched alkylene radical having 1 to 8 C atoms, an o-, m- or p-phenylene radical or a radical of the formula V

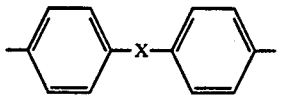

wherein X can be —CH$_2$—, —C(CH$_3$)$_2$—, —O—, —S—, or —SO$_2$—, and Ar denotes a radical of the formula VI

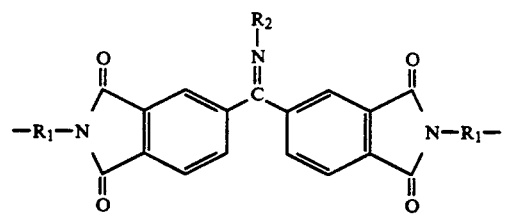

in which R$_1$ and R$_2$ are as defined above, and polyamides of the formula VII

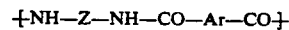

in which Ar and Z are as defined above.

The polymers can be prepared by solution polycondensation in a diluent which is inert under the reaction conditions, such as, for example, DMA, HMP or NMP.

Polyesters of the formula IVa are prepared from the Schiff's bases of the formula I according to the invention in which Y denotes hydroxyl by reaction with equimolar amounts of dicarboxylic acid dichlorides, such as, for example, isophthaloyl dichloride (IPDCL) or terephthaloyl dichloride (TPDCL).

To prepare polyesters of the formula IVb from Schiff's bases of the formula I in which Y denotes carboxyl, the carboxyl group must be activated, for example by conversion into the corresponding dicarboxylic acid dichlorides, anhydrides or esters. The desired polyesters of the formula IVb are then prepared from the dicarboxylic acid dichlorides by reaction with diols, such as, for example, ethylene glycol, hydroquinone or bisphenol A.

To prepare the polyamides of the formula VII, the Schiff's bases of the formula I in which Y denotes carboxyl are likewise converted into the corresponding dicarboxylic acid dichlorides by reaction with thionyl chloride, and these are then reacted with an equimolar amount of a diamine, such as, for example, bis-(4-aminophenyl)methane (MDA).

In cases where the dicarboxylic acid dichloride is reacted with a diol or a diamine, it is necessary to remove the hydrochloric acid formed. This is advantageously effected by addition of an equivalent amount of a suitable base, such as, for example, triethylamine, pyridine or dimethylaniline.

The reaction temperature is between −30° C. and 50° C., depending on the Schiff's base used and the polymer desired.

If appropriate, the reaction is carried out under a nitrogen atmosphere.

The polymers can be isolated by customary methods, for example by precipitation with water or other suitable diluents.

The polyesters and polyamides are distinguished by a very high heat stability and low glass transition temperature, which enables thermoplastic processing. The production of films and fibers is facilitated by the excellent solubility in DMA.

Example 1 a) Preparation of N,N'-bis(hydroxyethyl)-3,3',4,4'-benzophenonetetracarboxylic acid diimide 20 g (0.062 mol) of BTDA were initially introduced into a three-necked flask with a magnetic stirrer, dropping funnel and thermometer and were dissolved in 180 ml of DMA, and 7.58 g (0.124 mol) of ethanolamine, dissolved in 20 ml of DMA, were slowly added dropwise from a dropping funnel. The reaction mixture was then stirred at room temperature for half an hour and subsequently heated under reflux for 2 hours.

For working-up, the reaction mixture was cooled to room temperature and poured onto 2 l of water. The crystals which had precipitated were then filtered off with suction, recrystallized from DMF/benzene =1:1 and dried to constant weight in a vacuum drying cabinet at 80° C.

Yield: 22.79 g (90% of theory)
Melting point: 208°–209° C.

b) Preparation of N,N'-bis(hydroxyphenyl)-3,3',4,4'-benzophenonetetracarboxylic acid diimide The reaction procedure was analogous to Example 1a), the product already precipitating after the start of the heating phase. The yellow crystals were filtered off with suction and, after recrystallization from DMF/benzene =1:1, were dried to constant weight in a vacuum drying cabinet at 80° C.

Yield: 27.21 g (87% of theory) yellow crystals
Melting point: 441° C.

Example 2 a) Preparation of the Schiff's base from N,N'-bis-(hydroxyethyl)-3,3',4,4'-benzophenonetetracarboxylic acid diimide and n-hexylamine 20 g (0.049 mol) of N,N'-bis(hydroxyethyl)-3,3',4,4'-benzophenonetetracarboxylic acid diimide were dissolved in 150 ml of absolute dimethylacetamide (DMA) under the influence of heat, and 24.78 g (0.245 mol) of n-hexylamine, dissolved in 30 ml of absolute toluene as an entraining agent for the water, were slowly added dropwise. Two spatula-tips of p-toluenesulfonic acid were then added to the reaction mixture as a catalyst and the temperature was kept between 120° C. and 130° C. for 24 hours.

The DMA was then distilled off in vacuo, together with the toluene and the water formed, the residue which remained was taken up in methylene chloride and the mixture was purified by extraction with water to remove the catalyst and residues of solvent. The organic phase was collected, dried over sodium sulfate and evaporated. The crude product thus obtained was purified by column chromatography.

Yield: 13.2 g (55% of theory) yellow liquid (1)

Products (3)–(7) were prepared analogously to Example 2a).

The elemental analyses and imine bands can be seen from Table 1.

b) Preparation of the Schiff's base of N,N'-bis(hydroxyethyl)-3,3',4,4'-benzophenonetetracarooxylic acid-diimide and hydroxylamine 15.14 g (0.074 mol) of hydroxylamine hydrochloride and 4.8 g (0.06 mol) of sodium acetate were dissolved in 30 ml of water, and the solution was heated to 60° C. 20 g (0.049 mol) of N,N'-bis(hydroxyethyl)-3,3',4,4'-benzophenonetetracarboxylic acid diimide were then slowly added dropwise. After 30 minutes, the reaction mixture was cooled to 0° C. and the oxime which had separated out was filtered off with suction. After purification by means of column chromatography, the yellow crystals were dried to constant weight at 60° C. in a vacuum drying cabinet.

Yield: 12.45 g (60% of theory) yellow crystals (2)
Melting point: 250°–253° C.

TABLE 1

Schiff's bases from the diimide $$HO-(CH_2)_2-N \cdots \text{[diimide with } R_2 \text{ on central } C=N\text{]} \cdots N-(CH_2)_2-OH$$

| No. | R$_2$ | Imine band (cm$^{-1}$) |
|---|---|---|
| 1 | —(CH$_2$)$_5$—CH$_3$ | 1616 |
| 2 | —OH | 1635 |
| 3 | —CH$_2$—COOH | 1608 |
| 4 | —(CH$_2$)$_2$—OH | 1635 |
| 5 | —NH—CO—NH—H$_5$C$_6$ | 1608 |
| 6 | —NH—CO—NH$_2$ | 1608 |
| 7 | —(CH$_2$)$_6$—NH$_2$ | 1635 |

| | % CALCULATED | | | | % FOUND | | | |
|---|---|---|---|---|---|---|---|---|
| No. | C | H | N | O | C | H | N | O |
| 1 | 65.98 | 5.95 | 8.55 | 19.53 | 65.65 | 6.20 | 8.50 | 19.65 |
| 2 | 59.56 | 4.05 | 9.93 | 26.45 | 59.50 | 4.20 | 9.68 | 26.62 |
| 3 | 59.36 | 4.11 | 9.03 | 27.50 | 59.30 | 4.75 | 9.01 | 27.54 |
| 4 | 61.19 | 4.69 | 9.31 | 24.81 | 60.70 | 4.72 | 9.24 | 25.34 |
| 5 | 62.10 | 4.28 | 12.93 | 20.68 | 62.02 | 4.45 | 13.04 | 20.49 |
| 6 | 56.77 | 4.11 | 15.05 | 24.06 | 56.63 | 4.23 | 15.01 | 24.13 |
| 7 | 64.02 | 5.97 | 11.06 | 18.95 | 63.94 | 6.09 | 11.34 | 18.63 |

A number of Schiff's bases were prepared from N,N'-bis(hydroxyphenyl)-3,3',4,4'-benzeophenetetracarboxylic acid diimide and N,N'-bis(carboxyphenyl)-3,3',4,4'-benzophenonetetracarboxylic acid diimide analogously to the compounds described in Examples 2a and 2b.

The elemental analyses and imine bands can be seen from Table 2 and Table 3.

TABLE 2

Schiff's bases from the diimide

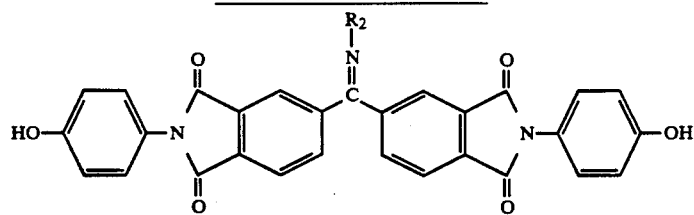

| No. | R₂ | Imine band (cm⁻¹) |
|---|---|---|
| 8 | —(CH$_2$)$_5$—CH$_3$ | 1608 |
| 9 | —OH | 1608 |
| 10 | —CH$_2$—COOH | 1616 |
| 11 | —(CH$_2$)$_2$—OH | 1635 |
| 12 | —NH—CO—NH—H$_5$C$_6$ | 1608 |
| 13 | —NH—CO—NH$_2$ | 1608 |
| 14 | —(CH$_2$)$_6$—NH$_2$ | 1635 |

| No. | % CALCULATED | | | | % FOUND | | | |
|---|---|---|---|---|---|---|---|---|
|  | C | H | N | O | C | H | N | O |
| 8 | 71.54 | 4.97 | 7.15 | 16.34 | 71.40 | 4.99 | 7.09 | 16.52 |
| 9 | 67.05 | 3.30 | 8.09 | 21.56 | 67.03 | 3.37 | 7.86 | 21.74 |
| 10 | 66.31 | 3.41 | 7.48 | 22.79 | 66.17 | 3.49 | 7.43 | 22.91 |
| 11 | 68.00 | 3.87 | 7.67 | 20.45 | 67.81 | 3.92 | 7.69 | 20.64 |
| 12 | 67.81 | 3.64 | 10.97 | 17.56 | 67.45 | 3.68 | 11.02 | 17.88 |
| 13 | 64.17 | 3.41 | 12.47 | 19.94 | 63.89 | 3.55 | 12.42 | 20.14 |
| 14 | 69.76 | 5.02 | 9.30 | 15.93 | 69.72 | 5.32 | 9.49 | 15.47 |

TABLE 3

Schiff's bases from the diimide

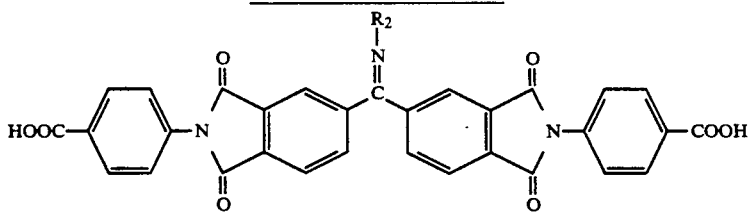

| No. | R₂ | Imine band (cm⁻¹) |
|---|---|---|
| 15 | —(CH$_2$)$_5$—CH$_3$ | 1616 |
| 16 | —OH | 1635 |
| 17 | —CH$_2$—COOH | 1608 |
| 18 | —(CH$_2$)$_2$—OH | 1635 |
| 19 | —NH—CO—NH—H$_5$C$_6$ | 1608 |
| 20 | —NH—CO—NH$_2$ | 1608 |
| 21 | —(CH$_2$)$_6$—NH$_2$ | 1635 |

| No. | % CALCULATED | | | | % FOUND | | | |
|---|---|---|---|---|---|---|---|---|
|  | C | H | N | O | C | H | N | O |
| 15 | 69.04 | 4.54 | 6.53 | 19.89 | 68.90 | 4.72 | 6.60 | 19.78 |
| 16 | 64.70 | 2.98 | 7.30 | 25.02 | 64.58 | 3.14 | 7.26 | 25.02 |
| 17 | 64.19 | 3.10 | 6.80 | 25.91 | 63.90 | 3.25 | 6.75 | 26.10 |
| 18 | 65.67 | 3.57 | 6.96 | 23.86 | 65.52 | 3.63 | 7.14 | 23.71 |
| 19 | 65.80 | 3.34 | 10.10 | 20.76 | 65.52 | 3.49 | 10.24 | 20.75 |
| 20 | 62.24 | 3.10 | 11.34 | 23.32 | 62.03 | 3.35 | 11.65 | 22.97 |
| 21 | 67.47 | 4.59 | 8.51 | 19.43 | 67.43 | 4.63 | 8.49 | 19.45 |

Example 3

Preparation of a polyester from N,N'-bis(hydroxyethyl)-3,3',4,4'-benzophenonetetracarboxylic acid diimide and isophthaloyl dichloride (IPDCL)

10 g (0.025 mol) of N,N'-bis(hydroxyethyl)-3,3',4,4'-benzophenonetetracarboxylic acid diimide and 5.08 g (0.025 mol) of IPDCL were dissolved in 50 ml of absolute DMA at room temperature. 5.75 g (0.057 mol) of triethylamine, dissolved in 10 ml of absolute DMA, were added dropwise as an acid-trapping agent to the reaction solution, which had been cooled to 0°-5° C. After addition of a further 0.5 ml of triethylamine, the viscous solution was stirred at 20° C. for 2.5 hours. The salt formed was filtered off, and the polymer was precipitated with water, centrifuged off, washed with water and dried to constant weight in a vacuum drying cabinet at 80° C.

Yield: 12.52 g (93% of theory) (22)

A number of other polyesters were prepared by the same method. Their glass transition temperatures, the intrinsic viscosities, the heat stabilities, the solubilities, the film-forming capacity and the elemental analyses are summarized in Table 4.

TABLE 4

| | Starting substances | | T | TGA | I.V. | |
|---|---|---|---|---|---|---|
| | Dichloride | Diol | °C. | °C. | dL/g | Sol. |
| 22 | IPDCL | V | 273 | 433 | 0.25 | + |
| 23 | IPDCL | 1 | 155 | 373 | 0.40 | + |
| 24 | IPDCL | 8 | 166 | 521 | 0.71 | + |
| 25 | IPDCL | 2 | 149 | 420 | 0.45 | + |
| 26 | IPDCL | 9 | 240 | 546 | — | — |
| 27 | IPDCL | 5 | 132 | 416 | 0.48 | + |
| 28 | IPDCL | 12 | 143 | 570 | 0.53 | + |
| 29 | IPDCL | 3 | — | 367 | 0.27 | + |
| 30 | IPDCL | 7 | — | 451 | 0.29 | + |
| 31 | TPDCL | 8 | — | 530 | 0.42 | + |
| 32 | TPDCL | 1 | — | 389 | 0.39 | + |
| 33 | TPDCL | 2 | 185 | 433 | — | — |
| 34 | TPDCL | 9 | — | 570 | — | — |
| 35 | TPDCL | 5 | 139 | 431 | 0.60 | + |
| 36 | TPDCL | 12 | 208 | 590 | 0.65 | + |

T: Glass transition temperature
TGA: Heat stability
I.V.: The intrinsic viscosity measured at 25° C. and a concentration of 0.5% by weight in DMA
Sol.: Solublility in DMA
V: Comparison substance: N,N'-bis(hydroxyethyl)-3,3',4,4'-benzophenonetetracarboxylic acid diimide

| | % CALCULATED | | | | % FOUND | | | |
|---|---|---|---|---|---|---|---|---|
| No. | C | H | N | O | C | H | N | O |
| 22 | 64.69 | 3.37 | 5.20 | 26.74 | 63.91 | 3.53 | 5.49 | 27.07 |
| 23 | 67.62 | 5.03 | 6.76 | 20.59 | 67.22 | 5.39 | 7.05 | 20.34 |
| 24 | 71.96 | 4.35 | 5.86 | 17.83 | 71.23 | 4.58 | 6.19 | 18.00 |
| 25 | 62.93 | 3.46 | 7.59 | 26.01 | 61.96 | 3.75 | 7.82 | 26.47 |
| 26 | 68.42 | 2.95 | 6.47 | 22.17 | 68.11 | 3.25 | 6.31 | 22.33 |
| 27 | 64.38 | 3.75 | 10.43 | 21.44 | 63.95 | 4.06 | 10.37 | 21.62 |
| 28 | 68.84 | 3.28 | 9.12 | 18.76 | 68.39 | 3.52 | 9.04 | 19.05 |
| 29 | 62.52 | 3.55 | 7.06 | 26.87 | 62.29 | 3.82 | 6.93 | 26.96 |
| 30 | 66.03 | 5.07 | 8.80 | 20.10 | 65.61 | 5.57 | 8.39 | 20.43 |
| 31 | 71.96 | 4.35 | 5.86 | 17.83 | 71.13 | 4.96 | 5.47 | 18.51 |
| 32 | 67.62 | 5.03 | 6.76 | 20.59 | 67.35 | 5.43 | 6.48 | 20.74 |
| 33 | 62.93 | 3.46 | 7.59 | 26.01 | 62.41 | 3.89 | 7.78 | 25.92 |
| 34 | 68.42 | 2.95 | 6.47 | 22.17 | 67.70 | 3.50 | 6.09 | 22.71 |
| 35 | 64.38 | 3.75 | 10.34 | 21.44 | 63.86 | 4.15 | 10.79 | 21.17 |
| 36 | 68.84 | 3.28 | 9.12 | 18.76 | 68.12 | 3.59 | 9.43 | 18.86 |

Example 4

Preparation of a polyamide from (15) and bis-(4-aminophenyl)methane (MDA)

1.9822 g (0.01 mol) of MDA were dissolved in a mixture of 25 ml of absolute N-methyl-2-pyrrolidone (NMP) and 50 ml of absolute hexamethylphosphoric acid triamide (HMP) at room temperature under a nitrogen atmosphere. The solution was cooled to $-15°$ C. and left to stand for 15 minutes. 6.8054 g (0.01 mol) of dicarboxylic acid dichloride (prepared from dicarboxylic acid (15) and thionyl chloride in absolute benzene; employed directly after preparation) were then added all at once. The reaction mixture was warmed slowly to room temperature and then stirred overnight under nitrogen. The viscous mass formed was poured into 500 ml of hot water, while stirring, and the polymer which had precipitated was comminuted, washed several times with water and dried to constant weight in vacuo at 80° C.

Yield: 7.49 g (93% of theory) (37)

All the other polyamides were prepared by the same method. Their glass transition temperatures, intrinsic viscosity, heat stability, solubility and elemental analysis are summarized in Table 5.

TABLE 5

| | Reaction partner | T °C. | TGA °C. | I.V. dL/g | Sol. |
|---|---|---|---|---|---|
| 37 | 15, MDA | 156 | 485 | 0.28 | + |
| 38 | 16, MDA | 251 | 535 | 0.34 | + |
| 39 | 19, MDA | 187 | 563 | 0.30 | + |

T: Glass transition temperature
TGA: Heat stability
I.V.: The intrinsic viscosity measured at 25° C. and a concentration of 0.5% by weight in DMA
Sol.: Solubility in DMA

| | % CALCULATED | | | | % FOUND | | | |
|---|---|---|---|---|---|---|---|---|
| No. | C | H | N | O | C | H | N | O |
| 37 | 74.52 | 4.88 | 8.69 | 11.91 | 74.03 | 5.25 | 8.37 | 12.35 |
| 38 | 71.64 | 3.69 | 9.49 | 15.18 | 71.09 | 3.98 | 9.32 | 15.61 |
| 39 | 71.57 | 3.89 | 11.46 | 13.09 | 71.12 | 4.16 | 11.39 | 13.33 |

What we claim is:

1. Compounds of the formula I

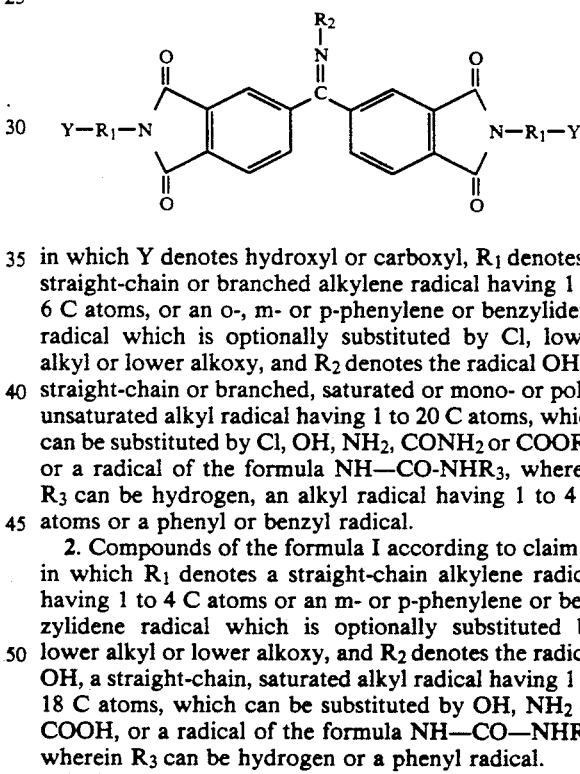

in which Y denotes hydroxyl or carboxyl, $R_1$ denotes a straight-chain or branched alkylene radical having 1 to 6 C atoms, or an o-, m- or p-phenylene or benzylidene radical which is optionally substituted by Cl, lower alkyl or lower alkoxy, and $R_2$ denotes the radical OH, a straight-chain or branched, saturated or mono- or polyunsaturated alkyl radical having 1 to 20 C atoms, which can be substituted by Cl, OH, $NH_2$, $CONH_2$ or $COOR_3$, or a radical of the formula $NH-CO-NHR_3$, wherein $R_3$ can be hydrogen, an alkyl radical having 1 to 4 C atoms or a phenyl or benzyl radical.

2. Compounds of the formula I according to claim 1, in which $R_1$ denotes a straight-chain alkylene radical having 1 to 4 C atoms or an m- or p-phenylene or benzylidene radical which is optionally substituted by lower alkyl or lower alkoxy, and $R_2$ denotes the radical OH, a straight-chain, saturated alkyl radical having 1 to 18 C atoms, which can be substituted by OH, $NH_2$ or COOH, or a radical of the formula $NH-CO-NHR_3$, wherein $R_3$ can be hydrogen or a phenyl radical.

3. Compounds of the formula I according to claim 1, in which $R_1$ denotes an ethylene or p-phenylene radical and $R_2$ denotes the radical OH, a straight-chain, saturated alkyl radical having 1 to 8 C atoms, which can be substituted by OH, $NH_2$ or COOH, or a radical of the formula $NH-CO-NHR_3$, wherein $R_3$ can be hydrogen or a phenyl radical.

* * * * *